United States Patent [19]

Metcalf

[11] Patent Number: 5,614,382
[45] Date of Patent: Mar. 25, 1997

[54] PLASMID FOR PRODUCTION OF CRM PROTEIN AND DIPHTHERIA TOXIN

[75] Inventor: Benjamin J. Metcalf, Rochester, N.Y.

[73] Assignee: American Cyanamid Company, Madison, N.J.

[21] Appl. No.: 450,333

[22] Filed: May 25, 1995

Related U.S. Application Data

[63] Continuation of Ser. No. 27,283, Mar. 5, 1993.
[51] Int. Cl.$^6$ .............................. C12P 21/06; C12N 1/20; C12N 15/03; C12N 15/63
[52] U.S. Cl. .................................... 435/69.1; 435/252.32; 435/320.1
[58] Field of Search .............................. 435/69.1, 252.32, 435/320.1

[56] References Cited

PUBLICATIONS

Archer et al., J. Gen. Microbiol., 139, 1753–1759 (1993).
Bishai et al., J. Bacteriol., 169, 5140–5151 (1987).
Cianciotto, J. Bacteriol., 168, 103–108 (1986).
Collier, Bacteriol. Revs., 39, 54–85 (1975).
Giannini et al., Nuc. Acids. Res., 12, 4063–4069 (1984).
Greenfield et al., Proc. Natl. Acad. Sci., USA, 80, 6853–6857 (1983).
Greenfield et al., Science, 238, 536–539 (Oct. 23, 1987).
Haynes et al., FEMS Microbiol. Letters, 61, 329–333 (1989).
Hemila et al., FEMS Microbiol. Letters, 65, 193–198 (1989).
Kaczorek et al., Science, 221, 855–858 (Aug. 26, 1983).
Maxwell et al., Molec. and Cell. Biol., 7, 1576–1579 (1987).
Pouwels et al., Cloning Vectors: A Laboratory Manual (Elsevier Science Pub. 1988).
Pugsley, Microbiol. Revs., 57, 50–108 (1993).
Simonen et al., Microbiol. Revs., 57, 109–137 (1993).
Uchida et al., J. Biol. Chem., 248, 3838–3844 (1973).
Uchida et al., J. Biol. Chem., 248, 3845–3850 (1973).
Uchida et al., J. Biol. Chem., 248, 3851–3854 (1973).
Rappuoli, R. 1983. Isolation and Characterization of *Corynebacterium diphtheriae*, Applied and Environ. Microbiol. 46:560–564.
Serwold–Davis, T.M, Groman, N.B., and Kao, C.C. 1990, Localization of an Origin of Replication in *Corynebacterium diphtheriae* Broad Host Range Plasmid pNG2 That Also Functions in *Escherichia coli*, 66:119–124.
Schafer, A., Kalinowski, J., Simon, R., Seep–Fieldhaus, A–H and Puhler., Alfred, 1990. High–Frequency Conjugal Plasmid Transfer From Gram–Negative *Escheriachia Coli* to Various Gram–Positive Coryneform Bacteria 1990 172(3):1663–1666.

*Primary Examiner*—George C. Elliott
*Assistant Examiner*—Thanda Wai
*Attorney, Agent, or Firm*—Alan M. Gordon; Alice O. Carroll

[57] ABSTRACT

The invention pertains to a novel method and plasmid system for producing abundant quantities of CRM197 protein, diphtheria toxin or other CRM proteins related to diphtheria toxin, as well as to microorganisms transformed with the novel plasmid. A particularly preferred DNA plasmid, designated pPX 3511, that combines the gene for CRM197 from the nontoxigenic betaphage and the plasmid pNG2-22 is described. The novel plasmid system is capable of transforming strains of *Corynebacterium diphtheriae* into strains which are capable of expressing high levels of the CRM197 protein without the use of multiple lysogens. The invention provides an elegant means for increasing protein production without having to manipulate the expression vector, such as by increasing the promoter strength, or removing the promoter from iron regulation.

12 Claims, 3 Drawing Sheets

PLASMID FOR PRODUCTION OF CRM PROTEIN AND DIPHTHERIA TOXIN

This is a continuation of copending application Ser. No. 08/027,283 filed on Mar. 5, 1993.

Background

The CRM197 protein is a nontoxic form of diphtheria toxin but is immunologically indistinguishable from the diphtheria toxin. CRM197 is produced by *C. diphtheriae* infected by the nontoxigenic phage β197$^{tox-}$created by nitrosoguanidine mutagenesis of the toxigenic corynephage β (Uchida, T. et al. 1971, *Nature New Biology* 233:8–11). The CRM197 protein has the same molecular weight as the diphtheria toxin but differs therefrom by a single base change (guanine to adenine) in the structural gene. This single base change causes an amino acid substitution (glutamic acid for glycine) in the mature protein and eliminates the toxic properties of diphtheria toxin. The CRM197 protein is a safe and effective T-cell dependent carrier for saccharides and is currently being used in the *Haemophilus influenzae* type b oligosacharide CRM197 conjugate vaccine (HibTiter™; Lederle Praxis Biologicals, Rochester, N.Y.).

Production of significant quantities of the CRM197 protein for use in vaccines has been hindered due to low protein abundance. Techniques have been developed to bolster the production of CRM proteins using double lysogens (Rappuoli, R., 1983, *Applied Env. Microbio.* 46:560–564; U.S. Pat. No. 4,925,792 issued to R. Rappuoli; and Rappuoli, R., 1983, *J. Bacteriol.* 153: 1202–1210) of the nontoxigenic corynephage β197. Rappuoli reports yields of CRM197 from double lysogens up to three fold higher than the single lysogens. The production Levels of CRM197 by single lysogens are adequate but economically unsatisfactory for the production of vaccines which utilize CRM197 protein.

Introduction of multiple lysogens of the corynephage β into *Corynebacterium diphtheriae* is a laborious screening process for identifying strains that can overproduce the CRM197 protein, diphtheria toxin or other CRM proteins that are cross-reactive with diphtheria toxin. In addition, this process is limited in its ability to manipulate protein expression using standard recombinant techniques. It would therefore be beneficial to develop a process that can generate significant quantities of diphtheria toxin and CRM proteins by increasing the gene copy number without the use of corynephage β; or by increasing the production levels of these proteins from strains lysogenic for corynephage β.

SUMMARY OF THE INVENTION

The invention pertains to a novel method and plasmid system for manipulating and introducing the gene encoding for CRM197, diphtheria toxin and other CRM proteins derived from the diphtheria toxin gene, as well as, to microorganisms transformed by these means. A particularly preferred DNA plasmid, designated pPX 3511, that combines the gene for CRM197 from the nontoxigenic betaphage and the plasmid pNG2-22 is described. The novel plasmid system is capable of transforming strains of *Corynebacterium diphtheriae* into strains which are capable of expressing high levels of the CRM197 protein without the use of multiple lysogens. The invention provides an elegant means for increasing protein expression of CRM197, diphtheria toxin, and other CRM proteins derived from the diphtheria toxin gene. Gene expression can also be manipulated by increasing the promoter strength or by removing the promoter from iron regulation. In preferred embodiments, the plasmid system can be used to express other proteins as genetic fusions with CRM197, diphtheria toxin or other CRM proteins derived from the diphtheria toxin gene. The regulatory and processing sequence from CRM197, diphtheria toxin or other CRM proteins derived from the diphtheria gene can be used to express foreign proteins in Corynebacterium spp.

DETAILED DESCRIPTION OF THE INVENTION

Figure 1:
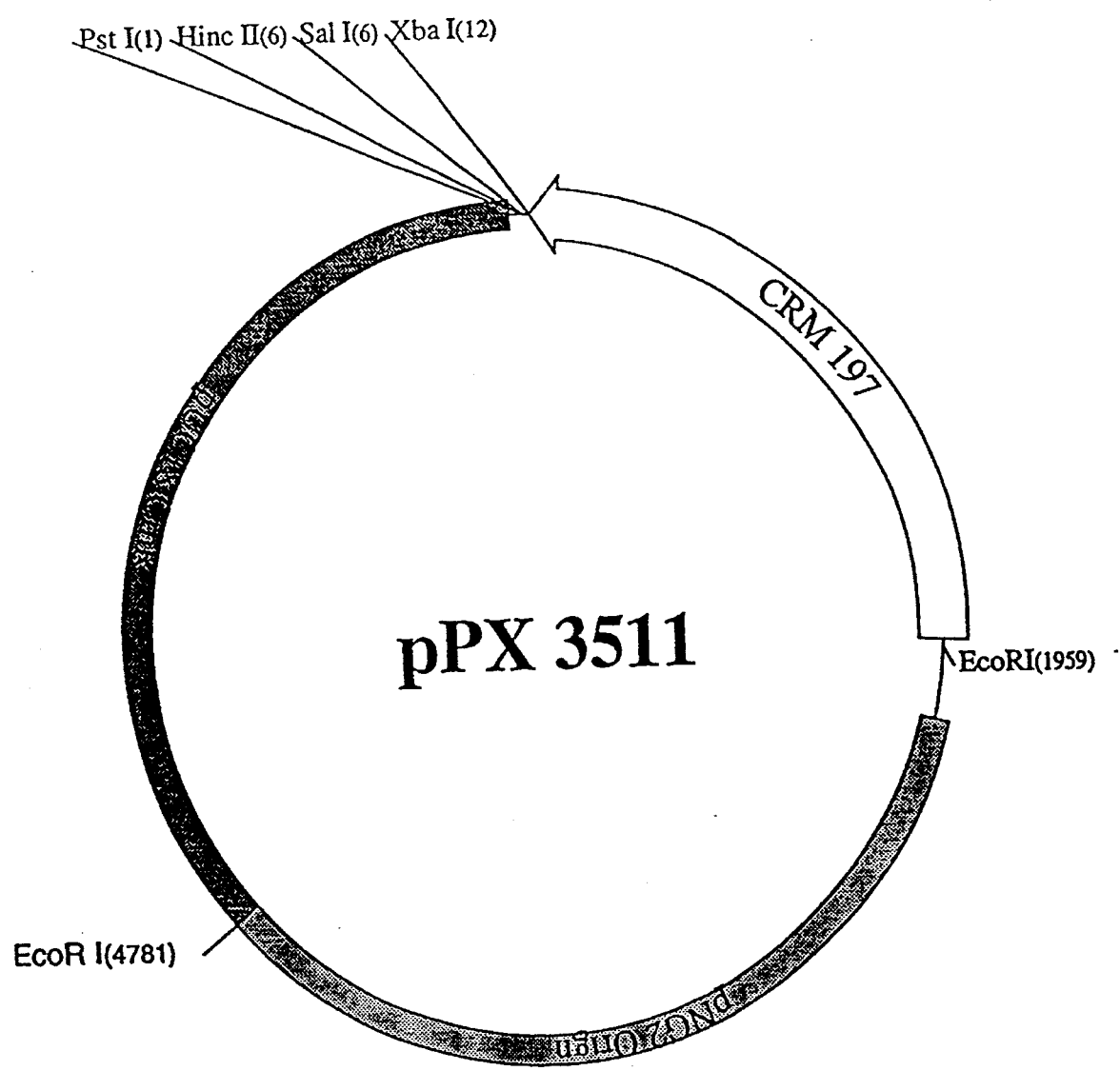
FIG. 1 is a recombinant DNA plasmid, designated pPX 3511, that contains the gene for CRM197, a multiple cloning site derived from *E. coli* cloning vector pUC 18 which contains the chloramphenicol resistance (CmR) marker and an origin of replication derived from plasmid pNG2-22 (Serwold-Davis, T. M. et al., 1990, *FEM Microbiol. Lett.* 66:119–124).

The invention pertains to a novel method and plasmid system for producing diphtheria toxin, CRM197 and other CRM proteins derived from the diphtheria toxin gene in quantities that are sufficient for use in vaccines or other use requiring adequate workable quantities of these proteins. The plasmid system provides an efficient means for introducing and increasing the copy number of the diphtheria toxin gene or CRM gene in Corynbacterium spp. The plasmid has its own independent episome with its own replication functions, thus enabling the plasmid to introduce extra copies of diphtheria toxin or CRM gene into host strains which are not capable of such integration or which have not been previously infected by phage β197$^{tox-}$. For example, the levels of CRM197 protein produced by Corynebacterium spp. harboring the plasmid of this invention are comparable, if not better, than yields of CRM197 protein expressed by multiple lysogens of *C. diphtheriae* that have been infected with the coryne-phage β197$^{tox-}$.

High level production plasmids of this invention comprise a gene encoding diphtheria toxin or CRM protein including its promoter and regulatory signal sequence; a Corynebacterium origin of replication such that the resultant plasmid can be introduced into Corynebacterium spp.; and a selectable marker that is optionally linked to a multiple cloning site. This plasmid is used to transform microorganisms of the species Corynebacterium, and particularly *Corynebacterium diphtheriae*, under conditions sufficient to facilitate expression of the diphtheria toxin or CRM gene. Suitable growth conditions are readily apparent to one skilled in the art depending upon the host organism. For instance, for optimal CRM197, diphtheria toxin or other CRM protein production from Corynebacterium spp., it is necessary to maintain the microorganism in a low iron or deferated medium.

The plasmid contains a gene encoding the diphtheria toxin or CRM protein that is derived from the diphtheria toxin gene. Examples of CRM proteins, i.e., Cross-Reacting Materials that are immunologically cross reactive with the diphtheria toxin, that can be used in the plasmid constructs of this invention include but are not limited to CRM197, CRM45, CRM30, CRM228 and CRM176. The gene encoding the CRM197 protein is derived from diphtheria toxin (DT), the sequence of which was reported by Greenfield et al. (Greenfield, L. et al., 1983, *Proc. Natl. Acad. Sci. USA*, 80:6853–6857). The difference between the DT gene and the CRM197 gene is a single base change in the structural gene. The nucleotide sequences for some of the CRM genes have been reported by Uchida, T. et al. (*J. Biol. Chem.*, 248:3838–3844, 1975). The entire CRM gene, including its regulatory signal sequence, can be produced by polymerase chain reaction (PCR). Other amplification techniques or synthetic techniques can be used to generate the CRM197 gene or other CRM genes.

The regulatory signal sequence on the gene encoding diphtheria toxin and CRM protein allows the protein to be secreted into the media. Thus, the secreted protein can be recovered from the media and purified using known techniques, such as salt precipitation and column chromatography.

The multiple cloning site is preferably derived from pUC 18, but multiple cloning sites derived from other sources can be used, for example pBluescript or other synthetic multiple cloning site. Alternatively, the multiple cloning site can be eliminated all together without interfering with the operability of the plasmid. In either instance, a selectable marker is incorporated into the plasmid. Any antibiotic resistance marker can be used as the selectable marker, such as but not limited to ampicillin, erythromycin, chloramphenicol, kanamycin. Susceptability of the corynebacter to the antibiotic of choice is tested first. Chloramphenicol is preferred if the expressed proteins are intended for human use since chloramphenicol has been approved for such purpose by the Food and Drug Administration. Other methods of plasmid selection such as heavy metal resistance or nutritional requirement can be used as alternatives to antibiotic resistance markers.

Origins of replication useful in constructing high production plasmids of this invention are those derived from Corynebacterium spp. The origin of replication chosen for pPX 3511 is derived from *Corynebacterium diphtheriae*. See Example Section. Other corynebacter origins of replication can be used.

In a preferred embodiment, high level expression of CRM197 protein is achieved Using a novel recombinant DNA plasmid, designated pPX 3511, capable of transforming strains of *C. diphtheriae* C7 into strains which produce high levels of CRM197 protein. Plasmid pPX 3511, shown in FIG. 1, contains the CRM197 gene derived from diphtheria toxin. (Greenfield, L. et al., 1983,*Proc. Natl. Acad. Sci. USA* 80:6853–6857). The remaining portion of the plasmid is derived from parent plasmid pNG2-22, into which the CRM197 gene is inserted.

Plasmid pPX 3511 is produced by first amplifying the CRM197 gene from *C. diphtheriae* by polymerase chain reaction (PCR). The CRM197 gene is then cloned into a *C. diphtheriae* plasmid containing a selectable marker, such as pNG2 (Schiller, J. et al., 1980, *Antimicrobial Agents and Chemotherapy* 8:814–821) and pNG2-22 (Serwold-Davis, T. M. et al., 1990, *FEM Microbiol. Lett.* 66:119–124). Both of these plasmids enjoy a broad host range and are capable of replicating in low copy number (5–10 copies/cell) in all coryneforms tested thus far.

Parent plasmid pNG2 is a naturally occurring *C. diphtheriae* plasmid that was originally isolated from erythromycin resistant clinical strains. The origin of replication for pNG2 is contained on a 2.6 kb EcoRI-ClaI fragment. This origin of replication has been used to create a chloramphenicol resistance vector designated, pNG2-22 (Serwold-Davis et al. Ibid.) and pCM 2.6 (Schmit, 1991, *Infect. Immun.* 59: 1899–1904 ).

Strain *C. diphtheriae* C7is then transformed with the resultant pPX 3511 plasmid by electroporation, thus enabling the bacterium to produce CRM197 without the presence of phage $\beta 197^{tox-}$. Other transformation techniques can be used such as known physical and chemical means (Serwold-Davis, et al., Ibid.). This technique of electrotransformation with pPX 3511 is also performed using *C. diphtheriae* C7 $(\beta 197)^{tox-}$ single lysogen to increase the production level of CRM197 protein. The levels of CRM197 protein expressed by the transformants are compared to expression levels from the single lysogen *C. diphtheriae* C7$(\beta 197)^{tox-}$ ATCC No. 53281 and the double lysogen *C diphtheriae* C7 $(\beta 197)^{tox-}$ M1, ATCC No. 39255, that does not harbor the pPX 3511 plasmid. It is observed that when plasmid pPX3511 is transfected into a *C. diphtheriae* C7 strain, the transformants are capable of expressing CRM197 at levels that are equivalent to *C. diphtheriae* double lysogen strains.

In other embodiments of the invention, the novel plasmid vector is modified to create a series of plasmid vectors with various capabilities. For example, site directed mutagenesis can be used to repair the single base change in CRM197, so that the new plasmid would express diphtheria toxin. Other changes can be made to the cloned CRM197 gene sequence to express other known diphtheria toxin CRM proteins, such as CRM45, CRM30, CRM228 and CRM176 (Uchida, T. et al. 1973, *J. Biol. Chem.* 248:3838–3844).

using recombinant DNA techniques, changes made to the diphtheria toxin regulatory or processing sequences of CRM197, or other similarly cloned diphtheria toxin or CRM genes can be used to further increase the production of these proteins. For example, the tox promoter region can be modified to free the promoter from iron regulation.

In another embodiment, the plasmid vector system can be modified to introduce restriction enzyme cloning sites into the amino terminus of the CRM197 gene or similarly cloned diphtheria toxin or CRM gene. Cloning the DNA sequences from other proteins into the cloning sites would then permit the plasmid vector to co-express other recombinant proteins or antigens as amino terminal fusions with the CRM197 protein or similarly cloned diphtheria toxin or CRM protein, all under the direction of the tox promoter and signal sequence. In addition to, or alternatively, cloning sites can be inserted into the carboxy terminal portion of the CRM197, diphtheria toxin or similarly cloned CRM to express other proteins as carboxy terminal fusions. Due to the presence of the CRM197 regulatory signal sequence, the resultant fusion protein would be secreted into the culture media. Alternatively, only the regulatory signal sequence of CRM197 need be used as a means for expressing secreted forms of other proteins into culture medium.

Suitable proteins and antigens useful in the production plasmid of the invention include particulate antigens, such as those derived from bacteria, viruses, parasites or fungi and microcomponents of cells and soluble antigens, such as proteins, peptides, hormones and glycoproteins. Antigens of particular interest are viral, fungal, parasite or bacterial antigens, allergens, autoimmunity related antigens, or tumor-associated antigens. The antigens can be obtained from natural sources or they can be produced by recombinant DNA technology or by other artificial means.

Among the bacterial antigens of interest are those associated with the human bacterial pathogens including, but not limited to for example, typable and nontypable *Haemophilus influenzae, Escherichia coli, Neisseria meningitidis, Streptococcus pneumoniae, Streptococcus pyogenes, Branhamella catarrhalis, Vibrio cholerae, Neisseria gonorrhoeae, Bordetella pertussis, Pseudomonas aeruginosa, Staphylococcus aureus, Klebsiella pneumoniae* and *Clostridium tetani*. Some specific bacterial antigens include bacterial surface and outer membrane proteins (e.g., from *Haemophilus influenzae, Neisseria meningitidis, Neisseria gonorrhoeae* or *Branhamella catarrhalis*) and bacterial surface proteins (e.g., the M protein from *Streptococcus pyogenes* or the 37 kilodalton surface protein from *Streptococcus pneumoniae*).

Viral antigens from pathogenic viruses include but are not limited to, human immunodeficiency virus (types I and II), human T-cell leukemia virus (types I, II and III), respiratory syncytial virus, hepatitis A, hepatitis B, hepatitis C, non-A and non-B hepatitis virus, herpes simplex virus (types I and II), cytomegalovirus, influenza virus, parainfluenza virus, poliovirus, rotavirus, coronavirus, rubella virus, measles virus, varicella, Epstein Barr virus, adenovirus, papilloma virus and yellow fever virus.

Several specific viral antigens of these pathogenic viruses include the F protein (especially antigens containing the F peptide 283–315, described in WO89/02935 entitled "Respiratory Syncytial Virus: Vaccines and Diagnostic Assays" by Paradiso, P. et al. ) and the N and G proteins of respiratory syncytial virus (RSV), VP4 (previously known as VP3 ), VP6 and VP7 polypeptides of rotavirus, envelope glycoproteins of human immunodeficiency virus, the surface and the presurface antigens of hepatitis B and herpes glycoproteins B and D.

Fungal antigens can be those derived from fungi including but are not limited to Candida spp. (especially albicans), Cryptococcus spp. (especially neoformans), Blastomyces spp. (e.g., dermatitidis), Histoplasma spp. (especially capsulatum), Coccidroides spp. (especially immitis), Paracoccidroides spp. (especially brasiliensis) and Aspergillus spp. Examples of parasite antigens include but are not limited to Plasmodium spp., Eimeria spp., Schistosoma spp., Trypanosoma spp., Babesia spp., Leishmania spp., Cryptosporidia spp., Toxoplasma spp. and Pneumocystis spp.

The invention will be further illustrated by the following non-limiting exemplification:

EXAMPLE 1

Constructs

Bacterial Strains

*E. coli* DH5α (BRL, Gaithersburg, Md.) is used for all cloning procedures. Strains of nontoxigenic, nonlysogenic *C. diphtheriae* C7 $(-)^{tox-}$, nontoxigenic, single lysogen *C. diphtheriae* C7 $(\beta 197)^{tox-}$ ATCC No. 53281 are used as both plasmid hosts and controls in CRM197 protein expression studies The nontoxigenic, double lysogen *C diphtheriae* C7($\beta$197)$^{tox-}$ ATCC No. 39255 issued as a control in CRM197 protein expression experiments.

Media and Conditions for Cultivation

*E. coli* DH5α is routinely grown on super optimal broth (SOB) agar medium and in SOB liquid at 37° C. (Sambrook, J. et al., 1989, *Molecular Cloning: A Laboratory Manual*, Cold Spring Harbor Laboratory Press, Cold Spring Harbor, N.Y.). *C. diphtheriae* C7 strains are routinely cultured on SOC agar (Sambrook, J. et al., Ibid. ) and liquid. ET osmotic agar medium (Best, G. R. and M. L. Britz, 1986, *Appl. Microbiol. Biotech.*, 23:288–293) is used when plating electroporated cells. Deferated CY medium (Rappuoli, R. et al., 1983, *J. Bacteriol.*, 153:1202) is used for experiments involving the expression of CRM197. Chloramphenicol is added at 34 μg/ml for *E. coli* DH5α and 2μg/ml for *C. diphtheriae* C7 strains containing plasmid pPX 3511.

Cloning of the CRM197 Gene

The CRM197 gene is cloned by PCR (polymerase chain reaction) amplification of the gone sequence from *C. diphtheriae* C7 ($\beta$197)$^{tox-}$ single lysogen DNA using oligonucleotide primers based on the published sequence of diphtheria toxin (Greenfield, L. et al., 1983, *Proc. Natl. Acad. Sci. USA* 80:6853–6857). The primers are designed so that one primer would create a SalI/HincII restriction site at the beginning of the functional gene and the other would make a XbaI site after the gene stop codon of the structural gene. These or similar primers are used to amplify and clone the CRM197 gene, the diphtheria toxin gone or any CRM gene similar to the diphtheria toxin gene encoded by the corynephage β.

The CRM197 PCR products are digested with HincII and XbaI and ligated into SmaI/XbaI digested pNG2-22, a broad host range chloramphenicol resistance vector with the ability to replicate in both *Escherichia coli* and Corynebacterium spp. The ligation is used to transform *E. coli* DH5α and recombinant colonies are screened by restriction analysis for the presence of the CRM197 gene. One isolate, pPX 3511, is sequenced using i overlapping primers to check for any changes to the CRM197 gene. The oligonucleotide primers used in PCR and sequencing are synthesized on an Applied Biosystems 380B DNA synthesizer. PCR is performed with a Perkin-Elmer Cetus DNA Thermal Cycler. Sequencing is performed using an Applied Biosystems Sequencer 373A. The resulting plasmid (pPX 3511) is transferred by electroporation into the nontoxigenic, non-lysogenic strain *C. diphtheriae* C7(–)$^{tox-}$ and the nontoxigenic strain *C. diphtheriae* C7 ($\beta^{197}$)$^{tox-}$, ATCC No. 53281.

Electroporation of *C. diphtheriae* C7

*C. diphtheriae* C7 is transformed with plasmid pPX-3511 DNA by electroporation using a protocol developed for the transformation of *Corynebacterium glutamicum* and *Brevibacterium lactofermentum* (Hayes, J. A. and M. L. Britz, 1989, *FEMS Microbiol. Lett.* 61:329–334), except that SOC medium supplemented with 0. 2% Tween-80 is used. A BTX Transfector 100 with Power Plus and Optimizor Graphic Pulse Analyzer and 1 mm gap cuvettes are used for electroporation. The presence of plasmid pPX 3511 in the transformed *C. diphtheriae* C7 strains is checked by plasmid rescue and restriction analysis.

EXAMPLE 2

Expression

Quantitative CRM$^{197}$ Expression Studies

Comparison of CRM197 production is made by growing strains of *C. diphtheriae* C7 under similar conditions and comparing the amount of CRM197 in the culture supernatant. In a quantitative comparison of the strains, 4 ml overnight cultures are diluted to an OD$_{600}$=0.1 in deferated CY medium (30 mL final volume in 250 ml Erlenmeyer flask) and grown shaking for 20 hours at 37° C. Strains containing pPX 3511 are grown both with and without antibiotic selection (2 μg/ml chloramphenicol). After incubation, the cultures are then centrifuged to remove the cells and 20 μl of the culture supernatants are run on a 12% SDS-PAGE gel. The gel is coomassie stained and quantitative comparison is made using a Bio-Rad Model 1650

Transmittance/Reflectance Scanning Densitometer with a Hoefer Scientific GS 370 Analysis Package. A comparison of the antigenic properties of the recombinant CRM197 protein and the lysogenic β197$^{tox-}$CRM197 protein is made by immunoblotting the gel and probing with monoclonal antibodies to CRM197. CRM197 produced by pPX 3511 is antigenically identical to CRM197 produced by lysogenic strains.

Plasmid pPX 3511 Stability Experiments

The stability of plasmid pPX 3511 is studied by using the maintenance of chloramphenicol resistance as an indicator of plasmid retention without antibiotic selection. Cultures of *C. diphtheriae* C7 (β197)$^{tox-}$pPX 3511 are grown in SOC broth supplemented with 0.1% Tween-80 to prevent cell clumping for 18 hours (14–17 generations) at 37° C. The cultures are then plated on SOC agar for colony counts and diluted 1/10 for the next generation. The SOC agar plates are replica-plated onto SOC agar 2µg/mL chloramphenicol and the percent of colonies maintaining chloramphenicol resistance is calculated. This process is repeated out to 60 generations.

EXAMPLE 3

Biological Results

Figure 2:
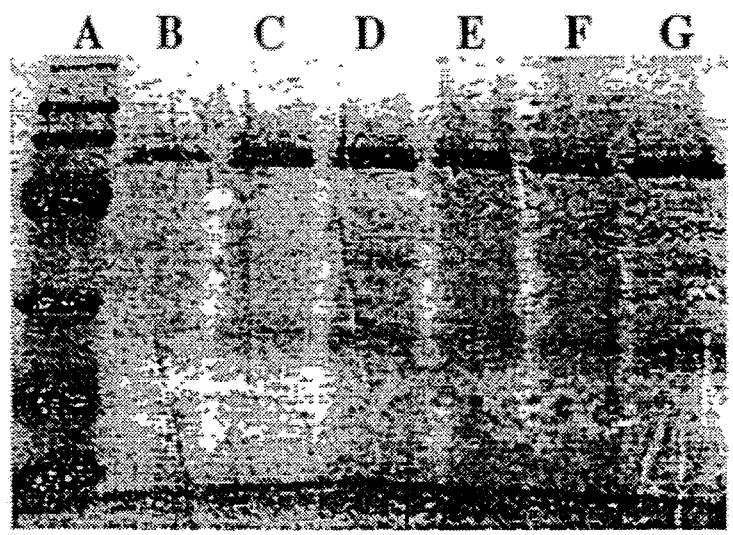
FIG. 2 is a 12% SDS-PAGE gel which shows the production of CRM197 (61.8 kilodaltons) from different strains of *C. diphtheriae* C7. Lane A: high molecular weight standards (BRL, 200–14.3 kilodaltons); Lane B: single lysogen C7(β197)$^{tox-}$; Lane C: double lysogen C7(β197)$^{tox-}$; Lane D: nonlysogenic C7(−)$^{tox-}$with pPX 3511, grown without chloramphenicol (Cm2) (2μg/ml); Lane E: nonlysogenic C7(−)$^{tox-}$with pPX 3511, grown with chloramphenicol (2μg/ml); Lane F: single lysogen C7(β197)$^{tox-}$with pPX 3511 grown without chloramphenicol (2μg/ml); Lane G: single lysogen C7(β197)$^{tox-}$grown with chloramphenicol (2μg/ml).
Figure 3:
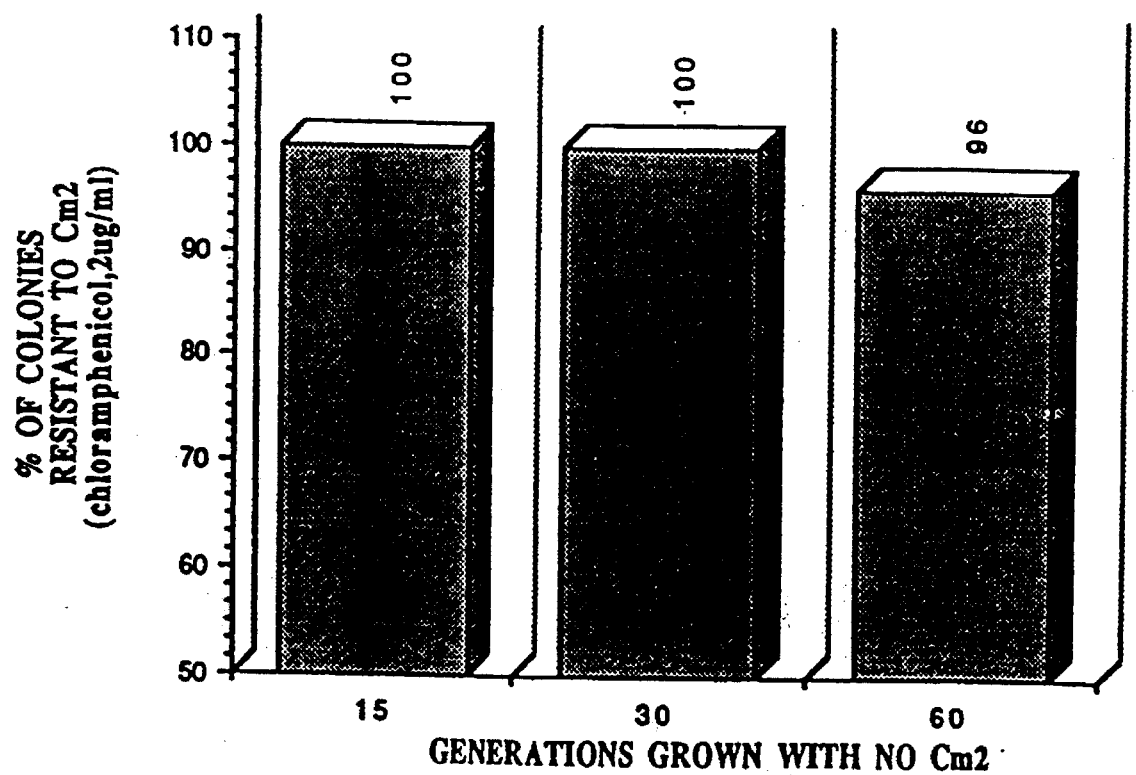
FIG. 3 shows the stability of plasmid pPX 3511 in *C. diphtheriae* C7 (β197)$^{tox-}$using chloramphenicol resistance as an indicator of plasmid retention without antibiotic selection.

The quantitative comparison of CRM197 production from the different *C. diphtheriae* C7 strains by densitometry of coomassie stained gels (FIG. 2) shows that the strains with pPX 3511 make about 2 times as much CRM197 as the single lysogen, and as much as the double lysogen (Table 1). The stability of plasmid pRX 3511 over sixty generations is shown in FIG. 3.

TABLE 1

Production of the CRM197 by *C. diphtheriae* C7 strains expressed as times greater than the single lysogen (β197)$^{tox-}$

|  | Times greater than Single lysogen (β197)$^{tox-}$ |
| --- | --- |
| Double lysogen (β197)$^{tox-}$ | 2.2 |
| pPX 3511(–)$^{tox-}$ no, Cm2 | 2.8 |
| pPX 3511(–)$^{tox-}$, Cm2 | 1.9 |
| pPX 3511 (β197)$^{tox-}$ no, Cm2 | 2.0 |
| pPX 3511 (β197)$^{tox-}$, Cm2 | 2.4 |

Biological Deposit

Plasmid pPX 3511 was deposited under the terms of the Budapest Treaty with the American Type Culture Collection (ATCC), 12301 Parklawn Drive, Rockville, Md. 20852 on Feb. 12, 1993 and has been assigned ATCC Accession Number 75415. All restrictions upon the availability to the public of the deposited material will be irrevocably removed upon granting of a patent on this application. The deposit will be maintained in a public depository for a period of at least 30 years from the date of deposit or for the enforceable life of the patent or for the period of five years after the date of the most recent request for the furnishing of a sample of the biological material, whichever is longer. The deposit will be replaced if it should become nonviable or nonreplicable.

Those skilled in the art recognize or are able to ascertain, using no more than routine experimentation, many equivalents to the specific embodiments of the invention described specifically herein. Such equivalents are intended to be encompassed in the scope of the following claims:

What is claimed is:

1. A method of producing diphtheria toxin or CRM protein that is cross reactive with diphtheria toxin, said method comprising: transforming a microorganism of the species *Corynebacterium diphtheria* strain C7 with a plasmid containing a a) gene encoding diphtheria toxin or CRM protein; b) a Corynebacterium origin of replication; and c) a selectable marker, and expressing said toxin or protein under conditions sufficient fox expression of the gene by the microorganism.

2. The method of claim 1 wherein the method of transformation is by electroporation.

3. The method of claim 1 wherein the gene encoding CRM is selected from the group consisting of CRM197, CRM45, CRM30, CRM228 and CRM176.

4. The method of claim 1 wherein the origin of replication is derived from Corynebacterium plasmid pNG2.

5. The method of claim 1 wherein the selectable marker is selected from the group Consisting of antibiotic resistance markers, heavy metal resistance markers and a gene regulated by a specific nutritional requirement.

6. The method of claim 1 further comprising a multiple cloning site which is operatively linked to the selectable marker.

7. The method of claim 4 wherein the multiple cloning site is derived from pUC18.

8. The method of claim 1 wherein the plasmid is pPX 3511, deposited as ATCC Accession No. 75415.

9. Plasmid pPX 3511 deposited as ATCC Accession No. 75415.

10. A microorganism of the species *Corynebacterium diphtheriae* strain C7 that is transformed with the plasmid of claim 7.

11. The microorganism of claim 10 that is *Corynebacterium diphtheriae* strain C7β197$^{tox-}$single lysogen.

12. A microorganism of the species *Corynebacterium diphtheriae* strain C7 that is transformed with the plasmid of claim 9.

* * * * *

UNITED STATES PATENT AND TRADEMARK OFFICE

(12)  CERTIFICATE EXTENDING PATENT TERM
UNDER 35 U.S.C. § 156

(68) PATENT NO.      : 5,614,382

(45) ISSUED          : March 25, 1997

(75) INVENTOR        : Benjamin J. Metcalf

(73) PATENT OWNER    : Wyeth Holdings Corporation

(95) PRODUCT         : Prevnar 13®

This is to certify that an application under 35 U.S.C. § 156 has been filed in the United States Patent and Trademark Office, requesting extension of the term of U.S. Patent No. 5,614,382 based upon the regulatory review of the product Prevnar 13® by the Food and Drug Administration. Since it appears that the requirements of the law have been met, this certificate extends the term of the patent for the period of

(94)                 1,217 days from March 25, 2014, the original expiration date of the patent, subject to the payment of maintenance fees as provided by law, with all rights pertaining thereto as provided by 35 U.S.C. § 156.

I have caused the seal of the United States Patent and Trademark Office to be affixed this 17th day of July 2015.

Michelle K. Lee
Under Secretary of Commerce for Intellectual Property and
  Director of the United States Patent and Trademark Office